(12) United States Patent
Morimoto et al.

(10) Patent No.: US 9,797,831 B2
(45) Date of Patent: Oct. 24, 2017

(54) ABSORPTION SPECTROMETER AND CALIBRATION CURVE PREPARATION METHOD THEREFOR

(71) Applicant: HORIBA, Ltd., Kyoto-shi, Kyoto (JP)

(72) Inventors: Yuichiro Morimoto, Kyoto (JP); Yoko Nakai, Kyoto (JP)

(73) Assignee: HORIBA, Ltd., Kyoto-shi, Kyoto (JP)

( * ) Notice: Subject to any disclaimer, the term of this patent is extended or adjusted under 35 U.S.C. 154(b) by 177 days.

(21) Appl. No.: 14/944,035

(22) Filed: Nov. 17, 2015

(65) Prior Publication Data
US 2016/0139057 A1 May 19, 2016

(30) Foreign Application Priority Data
Nov. 17, 2014 (JP) .................................. 2014-233025

(51) Int. Cl.
| | | |
|---|---|---|
| *G01J 3/46* | (2006.01) | |
| *G01N 21/359* | (2014.01) | |
| *G01N 21/27* | (2006.01) | |
| *G01N 21/85* | (2006.01) | |
| *G01N 21/3577* | (2014.01) | |
| *G01N 21/84* | (2006.01) | |

(52) U.S. Cl.
CPC ......... *G01N 21/359* (2013.01); *G01N 21/274* (2013.01); *G01N 21/3577* (2013.01); *G01N 2021/8405* (2013.01); *G01N 2021/8592* (2013.01)

(58) Field of Classification Search
CPC ........ G01N 21/33; G01N 21/27; G01N 21/85; G01N 21/65; G01N 21/658; G01N 21/274; G01N 21/359; G01J 3/02; G01J 3/46; G01J 3/50; G01J 3/51; G01J 3/52
See application file for complete search history.

(56) References Cited

U.S. PATENT DOCUMENTS

2004/0101908 A1* 5/2004 Fukuoka ............ G01N 21/3577
435/7.1

FOREIGN PATENT DOCUMENTS

JP H10030982 A 2/1998

* cited by examiner

*Primary Examiner* — Abdullahi Nur
(74) *Attorney, Agent, or Firm* — Alleman Hall Creasman & Tuttle LLP

(57) ABSTRACT

The present invention intends to reduce a measurement error in the concentration of a component due to the effect of the grain concentration of grain dispersion liquid. Also, the present invention is one that calculates the concentration of a predetermined component added into grain dispersion liquid in which grains are dispersed in liquid, with use of a light absorption spectrum obtained by irradiating the grain dispersion liquid with light and a preliminarily prepared calibration curve representing the relationship between a light absorption spectrum and the concentration of the predetermined component. Further, the calibration curve is prepared on the basis of multiple light absorption spectra obtained by measuring light absorption spectra of multiple grain dispersion liquids having mutually different grain concentrations for each of mutually different multiple concentrations of the predetermined component.

6 Claims, 3 Drawing Sheets

ABSORPTION SPECTROMETER AND CALIBRATION CURVE PREPARATION METHOD THEREFOR

TECHNICAL FIELD

The present invention relates to an absorption spectrometer that, in accordance with absorption spectrometry, analyzes the concentration of a predetermined component contained in grain dispersion liquid in which grains are dispersed in liquid, and to a method for preparing a calibration curve used for the absorption spectrometer.

BACKGROUND ART

As planarization techniques for semiconductor devices in semiconductor manufacturing processes, CMP (chemical mechanical polishing) methods are used. The CMP methods include a method that performs polishing while supplying slurry in which abrasive grains are dispersed in liquid.

In order to make it easy to polish a film formed on a semiconductor device, slurry added with an oxidizing agent such as hydrogen peroxide ($H_2O_2$) is used.

The addition amount of the oxidizing agent, i.e., the concentration of the oxidizing agent in the slurry is required to be highly accurately adjusted corresponding to a polishing target, polishing condition, or the like. In recent years, in particular, metal wiring has been formed as ultrafine patterns in association with increases in density, integration, and function of a semiconductor device, and in order to more highly accurately polish metal wiring parts, it is necessary to more highly accurately adjust the concentration of the oxidizing agent added to the slurry.

Note that conventionally the concentration of an oxidizing agent added to slurry has been measured by analyzing the concentration of the oxidizing agent in accordance with near-infrared spectroscopy using an absorption spectrometer as disclosed in Patent Literature 1.

CITATION LIST

Patent Literature

Patent Literature 1; Japanese Unexamined Patent Publication JP-A-10-30982

SUMMARY OF INVENTION

Technical Problem

In practice, when analyzing the concentration of an oxidizing agent added to slurry using a conventional absorption spectrometer, on the assumption that grain concentration of the slurry is constant, an optical absorption spectrum is measured for each of mutually different multiple component concentrations, and a calibration curve is prepared using the resulting multiple optical absorption spectra.

However, the present inventor has found that the concentration of grains (abrasive grains) dispersed in slurry is somewhat different from a specification value due to the difference in slurry lot, uneven distribution of the grains, or the like, and the effect of light scattering due to the grains in the slurry gives rise to a measurement error in the concentration of an oxidizing agent obtained by a conventional absorption spectrometer.

Therefore, the present invention is made in order to solve the above-described problem on the basis of the finding by the present inventor, and a main intended object thereof is to reduce a measurement error in the concentration of a measuring target component due to the effect of grain concentration of grain dispersion liquid.

Solution to Problem

That is, an absorption spectrometer according to the present invention is one that calculates the concentration of a predetermined measuring target component added into grain dispersion liquid in which grains are dispersed in liquid, with use of a light absorption spectrum obtained by irradiating the grain dispersion liquid with light and a preliminarily prepared calibration curve representing the relationship between a light absorption spectrum and the concentration of the measuring target component. Also, the calibration curve is prepared on the basis of multiple light absorption spectra obtained by measuring light absorption spectra of multiple grain dispersion liquids having mutually different grain concentrations for each of mutually different multiple concentrations of the measuring target component. Further, the absorption spectrometer is characterized by using the calibration curve to reduce the effect of the grain concentration of the grain dispersion liquid on the measurement of the concentration of the measuring target component.

Also, a calibration curve preparation method for an absorption spectrometer according to the present invention is a calibration curve preparation method for an absorption spectrometer that calculates the concentration of a predetermined component added into grain dispersion liquid in which grains are dispersed in liquid, with use of a light absorption spectrum obtained by irradiating the grain dispersion liquid with light and a preliminarily prepared calibration curve representing the relationship between a light absorption spectrum and the concentration of the predetermined component, and includes: a spectrum measuring step of measuring light absorption spectra of multiple grain dispersion liquids having mutually different grain concentrations for each of mutually different multiple concentrations of the predetermined component; and a calibration curve preparation step of preparing the calibration curve on the basis of the multiple light absorption spectra obtained by the spectrum measuring step.

Typically, the grain dispersion liquid is polishing liquid in which polishing grains are dispersed in liquid, and the measuring target component added into the grain dispersion liquid is an oxidizing agent.

Advantageous Effects of Invention

According to the present invention configured as described, since the calibration curve is prepared on the basis of the multiple light absorption spectra obtained by measuring the light absorption spectra of the multiple grain dispersion liquids having mutually different grain concentrations for each of the multiple concentrations of the measuring target component, a measurement error in the concentration of the measuring target component due to the effect of the grain concentration of the grain dispersion liquid can be reduced.

DESCRIPTION OF EMBODIMENTS

In the following, one embodiment of an absorption spectrometer according to the present invention will be described with reference to the drawings.

An absorption spectrometer 100 in the present embodiment is one that analyzes the concentration of a predetermined measuring target component added into grain dispersion liquid in which grains are dispersed in liquid, using absorption spectrophotometry.

The absorption spectrometer 100 in the present embodiment is one that analyzes the concentration of an oxidizing agent added into slurry of a CMP polishing apparatus used in a semiconductor manufacturing process, using near-infrared absorption spectrophotometry. By using the near-infrared absorption spectrophotometry, near-infrared light is absorbed by the measuring target component without being easily affected by scattering due to grains dispersed in the slurry, and therefore the concentration of the measuring target component can be accurately measured. Note that the slurry is different depending on a polishing target, in which solid grains such as $SiO_2$, $Al_2O_3$, $CeO_2$, $Mn_2O_3$, or diamond grains as abrasive grains are dispersed in a dispersion medium such as water or any of other chemical solutions. Also, the oxidizing agent is, for example, hydrogen peroxide ($H_2O_2$).

Figure 1:
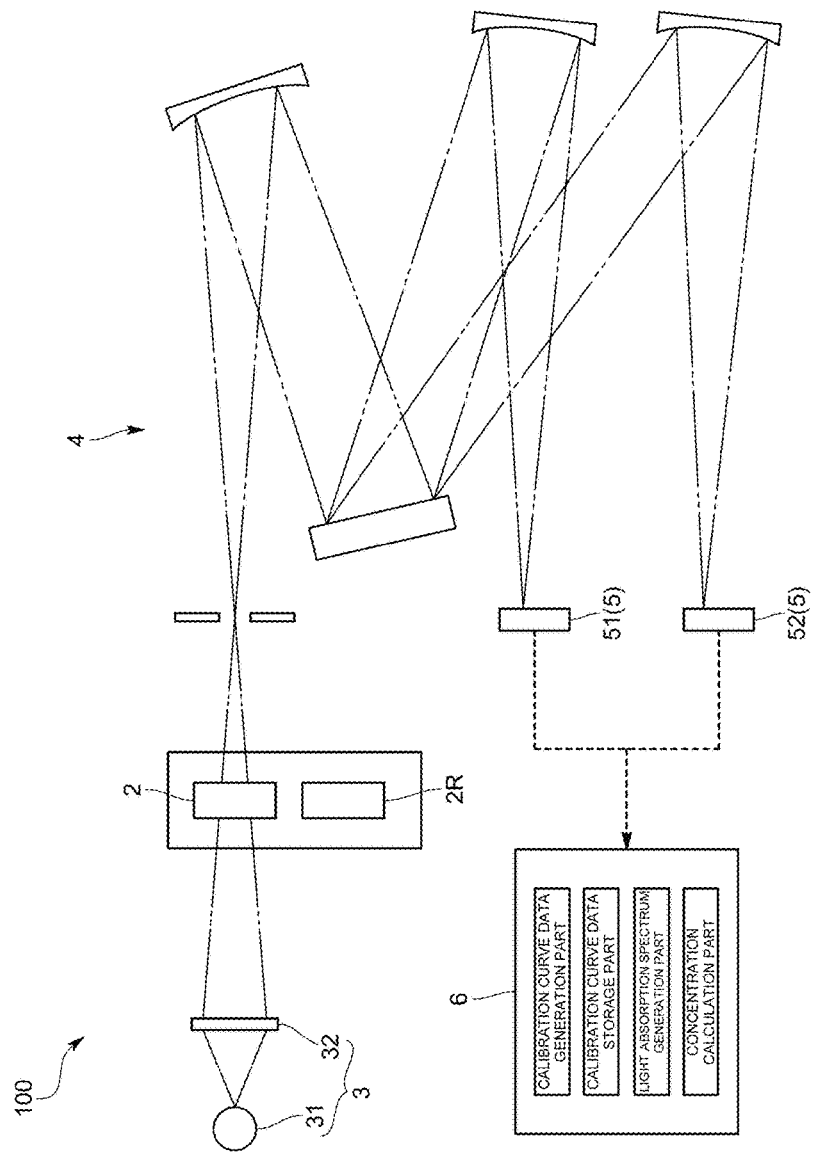
FIG. 1 is a schematic diagram illustrating a configuration of an absorption spectrometer in the present embodiment.

Specifically, as illustrated in FIG. 1, the absorption spectrometer 100 includes: a measuring cell 2 into which the slurry of the CMP polishing apparatus is introduced; a light irradiation part 3 that irradiates the measuring cell 2 with the near-infrared light; a spectroscope 4 that disperses the near-infrared light transmitting through the measuring cell 2; a light detector 5 that detects lights resulting from the dispersion by the spectroscope 4; and an arithmetic unit 6 that generates a light absorption spectrum (absorbance spectrum) from light intensity signals obtained by the light detector 5, and uses the light absorption spectrum to calculate the concentration of the oxidizing agent.

The absorption spectrometer 100 in the present embodiment includes a reference cell 2R separately from the measuring cell 2, and is configured to be able to switch a cell positioned in a light passing area (on a light path) where the light from the light source 3 passes to any of the measuring cell 2 and the reference cell 2R.

The light irradiation part 3 has: a continuous spectrum light source 31 including a lamp such as a halogen lamp; and a light collecting optical system 32 (light collecting lens) provided in a light irradiation direction of the light source 31.

The spectroscope 4 is one that disperses the light passing through the measuring cell 2 (or the reference cell 2R) to collect the resulting lights at an ultra-violet light detector 51 and a near-infrared light detector 52 included in the light detector 5. Note that the ultra-violet light detector 51 and the near-infrared light detector 52 are multichannel detectors.

The arithmetic unit 6 is one that operates a light absorption spectrum using light intensity signals at respective wavelengths obtained by the light detector 5, and from a light absorption spectrum obtained by actual measurement and a preliminarily prepared calibration curve, calculates the concentration of the oxidizing agent.

Note that the calibration curve is one representing the relationship between the light absorption spectrum and the concentration of the oxidizing agent, and calibration curve data indicating the calibration curve is stored in a calibration curve data storage part set in a predetermined area of a memory of the arithmetic unit 6.

Figure 2:
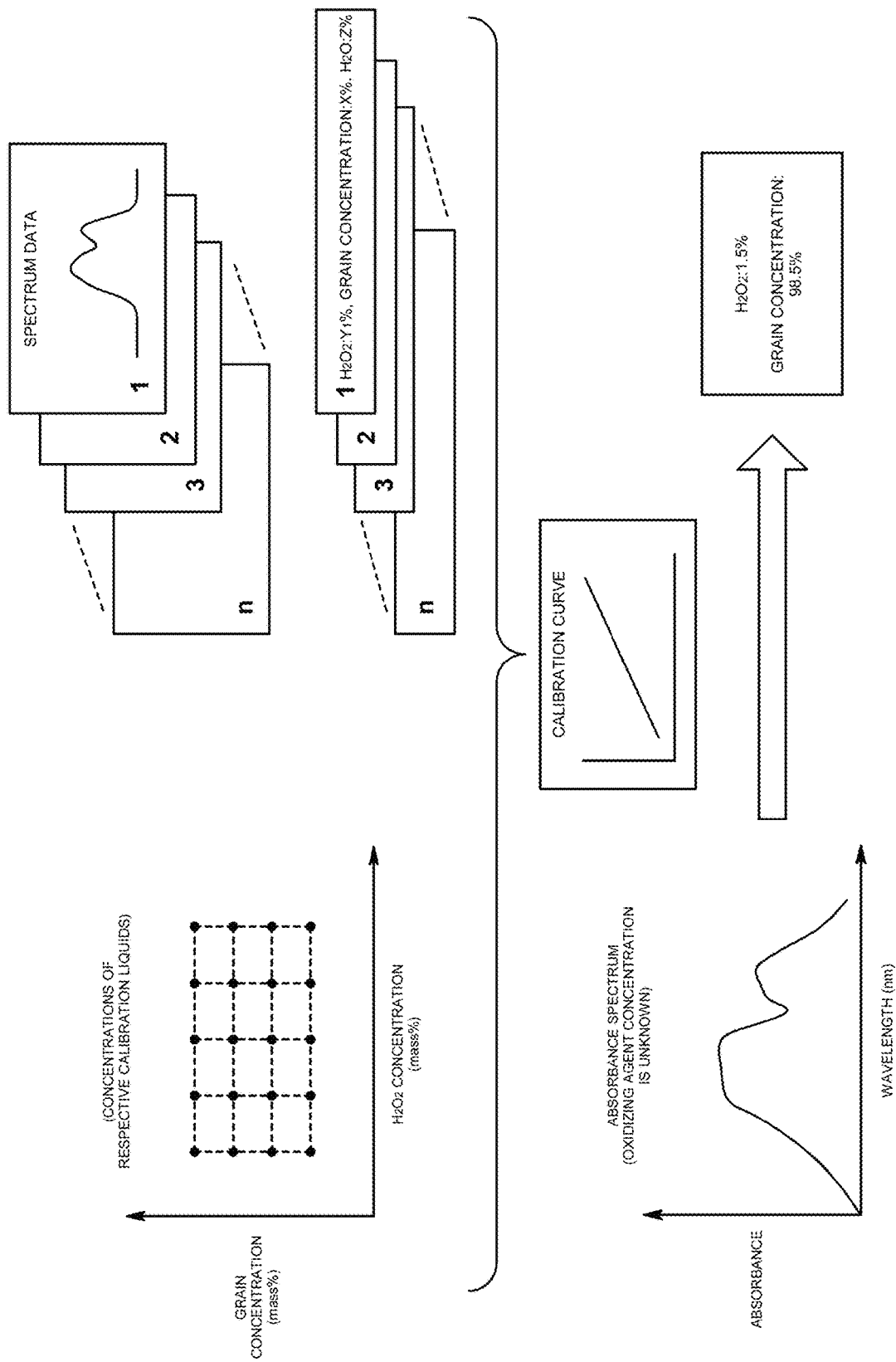
FIG. 2 is a schematic diagram illustrating a calibration curve preparation procedure.

Also, the calibration curve is one that was prepared by as illustrated in FIG. 2, measuring light absorption spectra of multiple types of slurries having mutually different grain concentrations for each of mutually different multiple oxidizing agent concentrations and performing multivariate analysis of the resulting multiple light absorption spectra.

Note that as the multivariate analysis, multiple regression analysis (MLR), principal component regression analysis (PCR), or partial least squares method (PLS) is possible.

Specifically, multiple types of slurries A to D having mutually different grain concentrations are prepared. That is, by adding the dispersion medium to undiluted slurry, grain concentration is variously adjusted as follows:

Slurry A: Undiluted slurry (grain concentration: X (%))

Slurry B: Undiluted slurry+Water (dispersion medium) (grain concentration: 0.95X (%))

Slurry C: Undiluted slurry+Water (dispersion medium) (grain concentration: 0.90X (%))

Slurry D: Undiluted slurry+Water (dispersion medium) (grain concentration: 0.85X (%))

(2) By adding the oxidizing agent to each of the slurries A to D so as to obtain mutually different oxidizing agent concentrations, multiple calibration liquids a to e are prepared.

For example, in the case of the slurry A, the following calibration liquids are prepared:

Calibration liquid Aa: Oxidizing-agent-added slurry A having an oxidizing agent concentration of $Y_1$ (%)

Calibration liquid Ab: Oxidizing-agent-added slurry A having an oxidizing agent concentration of $Y_2$ (%)

Calibration liquid Ac: Oxidizing-agent-added slurry A having an oxidizing agent concentration of $Y_3$ (%)

Calibration liquid Ad: Oxidizing-agent-added slurry A having an oxidizing agent concentration of $Y_4$ (%)

Calibration liquid Ae: Oxidizing-agent-added slurry A having an oxidizing agent concentration of $Y_5$ (%)

As with the slurry A, the other slurries B, C, and D are also added with the oxidizing agent to prepare calibration liquids Ba, Ca, and Da having an oxidizing agent concentration of $Y_1$ (%), calibration liquids Bb, Cb, and Db having an oxidizing agent concentration of $Y_2$ (%), calibration liquids Bc, Cc, and Dc having an oxidizing agent concentration of $Y_3$ (%), calibration liquids Bd, Cd, and Dd having an oxidizing agent concentration of $Y_4$ (%), and calibration liquids Be, Ce, and De having an oxidizing agent concentration of $Y_5$ (%).

(3) The light absorption spectra of the respective calibration liquids Aa to Ae, Ba to Be, Ca to Ce, and Da to De are measured. During the measurement, the arithmetic unit 6 relates data on each light absorption spectra, and grain concentration data and oxidizing concentration data on a calibration liquid of which the light absorption spectrum is measured to each other, and stores them in the memory. Alternatively, the arithmetic unit 6 may relate the light absorption spectrum data and the oxidizing concentration data to each other, and store them in the memory without the grain concentration data.

(4) A calibration curve data generation part of the arithmetic unit 6 performs the multivariate analysis of the multiple light absorption spectra obtained in (3) above, and thereby prepares the single calibration curve regardless of grain concentration. Further, the calibration curve data indicating the calibration curve is stored in the calibration curve data storage part.

Figure 3:
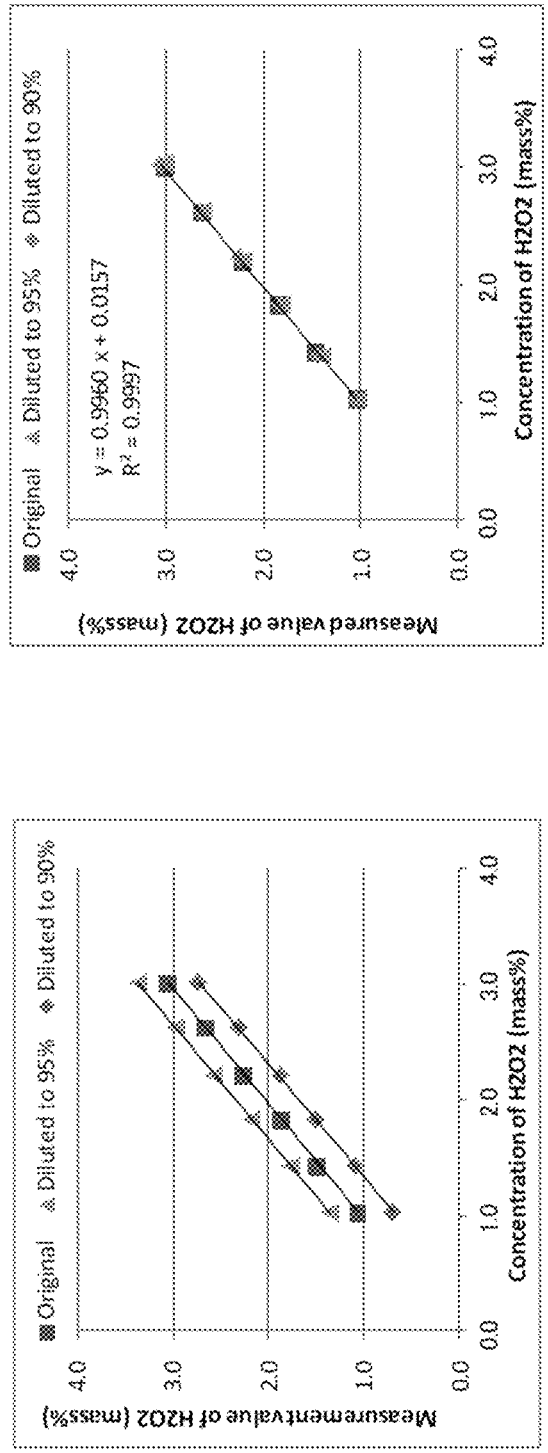
FIG. 3 is a diagram illustrating calibration curves obtained in accordance with a conventional manner and the present invention, respectively.

The calibration curve prepared in this manner is, for example, one illustrated in FIG. 3B. Note that calibration curves illustrated in FIG. 3A are ones prepared in a conventional manner using slurry having single grain concentration, and the calibration curves respectively at grain concentrations of X (%), 0.95X (%), and 0.90X (%) are different from one another.

Since the calibration curve is prepared on the basis of the multiple light absorption spectra obtained by measuring the light absorption spectra of the multiple slurries having mutually different grain concentrations for each of the multiple oxidizing agent concentrations, the absorption spectrometer 100 configured as described above can reduce a measurement error in the concentration of the oxidizing agent due to the effect of slurry grain concentration.

Also, by using the calibration curve in the present embodiment, not only the concentration of the oxidizing agent but grain concentration can also be calculated from a light absorption spectrum obtained by actual measurement and the calibration curve.

Note that the present invention is not limited to the above-described embodiment.

(1) Variation 1 (Background Correction)

For example, it may be configured to, when preparing the calibration curve, measure a light absorption spectrum (background spectrum) of the slurry without the addition of the oxidizing agent, and by performing multivariate analysis of subtracted light absorption spectra obtained by subtracting the background spectrum from the respective light absorption spectra, prepare the calibration curve. In this case, in actual measurement as well, concentration is calculated using a light absorption spectrum obtained by subtracting the spectrum of the pure slurry without the addition of the oxidizing agent from an obtained light absorption spectrum as a background. Note that in the method using the background correction, the slurry used to prepare the calibration curve and the slurry used for the actual measurement are not required to be the same. For example, the slurry used to prepare the calibration curve and the slurry used for the actual measurement may be different in grain size, solid concentration, pH, chemical composition, or the like. Further, the calibration curve may be prepared using water in place of the slurry. That is, it may be configured to measure a light absorption spectrum (background spectrum) of water without the addition of the oxidizing agent, and by performing multivariate analysis of subtracted light absorption spectra obtained by subtracting the background spectrum from respective light absorption spectra of waters added with the oxidizing agent at respective concentrations, prepare the calibration curve. In this case, in actual measurement of a sample in which the oxidizing agent is added into the slurry, concentration is calculated using a light absorption spectrum obtained by subtracting the light absorption spectrum of the pure slurry without the addition of the oxidizing agent from an obtained light absorption spectrum.

(3) Variation 2 (Differential→Multivariate Analysis)

Further, it may be configured to differentiate multiple light absorption spectra obtained from multiple calibration liquids to operate differential spectra, and by performing multivariate analysis of the differential spectra, prepare the calibration curve. In this case, in actual measurement as well, an obtained light absorption spectrum is differentiated to operate a differential spectrum, and concentration is calculated from the differential spectrum and the calibration curve. This configuration makes it possible to improve the measurement accuracy of oxidizing agent concentration. Also, by using the differential spectra, spectra based on the shapes of the light absorption spectra can be formed, and a shift due to the effect of slurry grain concentration can be cancelled.

The above-described embodiment is configured to measure the concentration of the predetermined measuring target component added into the slurry used in the semiconductor manufacturing process, but may be configured to measure the concentration of a predetermined measuring target component added into grain dispersion liquid that falls within the category of food such as milk.

Besides, it goes without saying that the present invention can be variously modified without departing from the scope thereof without limitation to any of the above-described embodiments.

REFERENCE SIGNS LIST

100: Absorption spectrometer
2: Measuring cell
3: Light source
4: Spectroscope
5: Light detector
6: Arithmetic unit

The invention claimed is:

1. An absorption spectrometer that calculates concentration of a predetermined measuring target component added into grain dispersion liquid in which grains are dispersed in liquid, with use of a light absorption spectrum obtained by irradiating the grain dispersion liquid with light and a preliminarily prepared calibration curve representing a relationship between a light absorption spectrum and concentration of the measuring target component, wherein
the calibration curve is prepared on a basis of multiple light absorption spectra obtained by measuring light absorption spectra of multiple grain dispersion liquids having mutually different grain concentrations for each of mutually different multiple concentrations of the measuring target component.

2. The absorption spectrometer according to claim 1, wherein
the calibration curve is prepared by performing multivariate analysis of the light absorption spectra.

3. The absorption spectrometer according to claim 1, wherein
the calibration curve is prepared by performing multivariate analysis of differential spectra obtained by differentiate the light absorption spectra.

4. The absorption spectrometer according to claim 1, obtaining the light absorption spectrum by irradiating the grain dispersion liquid with near-infrared light.

5. The absorption spectrometer according to claim 1, wherein
the grain dispersion liquid is polishing liquid in which polishing grains used in a semiconductor manufacturing process are dispersed in liquid, and
the measuring target component added into the grain dispersion liquid is an oxidizing agent.

6. A calibration curve preparation method for an absorption spectrometer that calculates concentration of a predetermined component added into grain dispersion liquid in which grains are dispersed in liquid, with use of a light absorption spectrum obtained by irradiating the grain dispersion liquid with light and a preliminarily prepared calibration curve representing a relationship between a light absorption spectrum and concentration of the predetermined component, the calibration curve preparation method comprising:
- a spectrum measuring step of measuring light absorption spectra of multiple grain dispersion liquids having mutually different grain concentrations for each of mutually different multiple concentrations of the predetermined component; and
- a calibration curve preparation step of preparing the calibration curve on a basis of the multiple light absorption spectra obtained by the spectrum measuring step.

* * * * *